United States Patent [19]

Horns et al.

[11] Patent Number: 5,227,542
[45] Date of Patent: Jul. 13, 1993

[54] PROCESS FOR THE PREPARATION OF SPHERICAL PARTICLES OF MAGNESIUM ALKOXIDE

[75] Inventors: Udo Horns, Theodore, Ala.; Thomas Jostmann, Dülmen, Fed. Rep. of Germany; Klaus-Dieter Kassmann, Marl, Fed. Rep. of Germany; Reinhard Matthes; Hartwig Rauleder, both of Rheinfelden, Fed. Rep. of Germany

[73] Assignee: Huels Aktiengesellschaft, Fed. Rep. of Germany

[21] Appl. No.: 938,511

[22] Filed: Sep. 1, 1992

Related U.S. Application Data

[63] Continuation of Ser. No. 641,140, Jan. 14, 1991, abandoned.

[30] Foreign Application Priority Data

Jan. 12, 1990 [DE] Fed. Rep. of Germany ....... 4000697

[51] Int. Cl.⁵ .............................................. C07C 31/30
[52] U.S. Cl. ................................................. 568/851
[58] Field of Search ........................................ 568/851

[56] References Cited

U.S. PATENT DOCUMENTS 4,663,299  5/1987  Chadurch et al. .................. 568/851

OTHER PUBLICATIONS

Weissberger, Separation and Purification, Interscience, 1956, pp. 821–822.

Primary Examiner—Marianne M. Cintins
Assistant Examiner—Rebecca Cook
Attorney, Agent, or Firm—Millen, White, Zelano & Branigan

[57] ABSTRACT

The invention involves spherical particles of magnesium alkoxide and a process for their preparation. Specifically, spherical magnesium alkoxide is produced by spray drying of an alcoholic solution of the corresponding carboxylated magnesium alkoxide and subsequent drying and decarboxylation, characterized in that the solution is sprayed via a two-material nozzle with inner atomization, which is operated in the part-load range at 10 to 30% of its capacity, into an inert accompanying gas which is under a pressure of 1.0 to 1.2 bar, has been preheated to 100°–140° C. and is fed cocurrently, after which the resulting finely divided carboxylated magnesium alkoxide is dried and is decarboxylated. The magnesium alkoxide is used for the preparation of a catalyst for the polymerization of α-olefins.

13 Claims, 1 Drawing Sheet

PROCESS FOR THE PREPARATION OF SPHERICAL PARTICLES OF MAGNESIUM ALKOXIDE

This application is a continuation of application Ser. No. 07/641,140, filed Jan. 14, 1991, now abandoned.

The present invention relates to finely divided, spherical magnesium alkoxide, a process for its preparation and its use for the preparation of highly active catalysts for the polymerization of o-olefins.

BACKGROUND OF THE INVENTION

Catalysts for olefin polymerization can be prepared by many processes, by reacting a solid component, which, as a rule, contains magnesium, titanium and a halogen, preferably chlorine, with an organoaluminium compound. The activity and the stereospecificity of such supported catalysts are usually improved by incorporating an electron donor (Lewis base) in the carrier component and by complexing the organoaluminium compound with an additional electron donor. It is known that magnesium alkoxides can be used as starting materials for the preparation of such supported catalysts. In this case, the magnesium alkoxide particles are preferably halogenated with the aid of a suitable halogenating agent, such as benzoyl chloride, thionyl chloride or titanium tetrachloride, in the presence of an electron donor, such as, for example, ethyl benzoate. If halogenating agents other than titanium tetrachloride are initially used, the latter must be incorporated in the solid component in the required amount of subsequent reaction with titanium tetrachloride, a content of 2 to 4.5% by weight of titanium usually being required. Regarding the details of the catalyst preparation, reference may be made to European Offenlegungsschrift 0,216,402 and 0,236,082 and to the literature cited there.

Since, in the polymerization of α-olefins, the morphology of the resulting polymer particles is a faithful reproduction of the morphology of the catalyst and this in turn is an exact image of that of the magnesium alkoxide used (see for example, J. Rudolph and J. Gross, Die Angewandte Makromolekulare Chemie 36 (1974), 195-197), it is also necessary to use a magnesium alkoxide of defined morphology to achieve defined properties of the desired polymer.

European Offenlegungsschrift 0,236,082 describes the preparation of spherical to raisin-shaped particles of magnesium alkoxides by conventional spray-drying. A preferably alcoholic solution of a carboxylated magnesium alkoxide is sprayed through a nozzle, which is not defined in detail, or via a rotating disk into a hot accompanying gas; this accompanying gas can be fed cocurrently or countercurrently. Although temperatures of 40° to 120° C. may be used, the range from 50° to 90° C. is preferred for ethanolic solutions since it is only in this range that the desired spherical to raisin-shaped particles can be produced. As is evident from the Examples, on the other hand, hollow spheres are obtained at 100°-120° C., many of which disintegrate into nutshell-like fragments.

Virtually all of the particles obtained by the process of European Offenlegungsschrift 0,236,082 have a diameter in the range of from 2 to 250 μm; preferably, 90% by volume of the particles are in the range from 10 to 40 μm, with a volume average at about 20 μm.

After spray drying, the bound $CO_2$ is expelled again by heating for several days in a stream of nitrogen at temperatures of, initially, 70° C. to, finally, 150° C. As an alternative to this expensive process, the carboxylated magnesium alkoxide obtained is said to be capable of being directed reacted further. The catalyst obtained is said to be capable of being used both for gas-phase polymerization and for liquid-phase polymerization. The process described in European Offenlegungsschrift 0,236,082 for the preparation of spherical particles of magnesium alkoxide is unsatisfactory for several reasons:

The preparation of more finely divided magnesium alkoxide having a mean diameter of less than 10 μm, as is desirable especially for the preparation of catalysts for the liquid-phase polymerization, is not possible by this method.

The relatively low drying temperature during spray drying leads to products which have a considerable residual moisture content, with the danger of agglomeration and caking on the walls.

An inconvenient aftertreatment is required to remove the bound $CO_2$. Alternatively, it is possible to dispense with this aftertreatment, but this gives a catalyst having substantially lower activity.

European Offenlegungsschrift 0,216,402 describes a multi-stage process for the preparation of spherical, mixed magnesium alkoxide of the formula $Mg(OR)_2$-$_a(OR')_a$ (a=0 to 0.5). In the preferred case ($R=C_2H_5$; $R'=CH_3$), the following procedure is adopted:

1) An ethanolic suspension of magnesium ethoxide is prepared from magnesium and ethanol; the product is isolated and dried.

2) The dried magnesium ethoxide is dissolved in methanol; the solution is spray-dried at 15° to 200° C., preferably at 30° to 70° C., spherical particles having a diameter of from 5 to 30 μm, preferably 10 to 18 μm, being formed. At this point, a mixed alkoxide predominantly containing methoxide groups is present; it is unsuitable in this form for the preparation of olefin polymerization catalysts.

3) The product from 2) is suspended in ethanol, and the methanol formed at the equilibrium is distilled off.

4) The product having a low content of methoxide groups is isolated and dried.

Apart from the many process stages, such as, for example, changing the solvent twice and drying three times, the low solubility of the magnesium ethoxide in methanol (see European Offenlegungsschrift 0,216,402, Example 1) and the resulting necessity to evaporate large amounts of solvent with corresponding consumption of energy, are found to be a serious disadvantage. Furthermore, the product still has a residual content of undesirable methoxide groups.

SUMMARY OF THE INVENTION

A primary aim of the present invention is to provide finely divided, spherical magnesium alkoxide for the preparation of a catalyst for the polymerization of α-olefins, which permits the production of polyolefins, in particular polypropylene, with high stereospecificity, high bulk density and good fluidizability during pneumatic conveying. The polymer should have as low an ash content as possible even without extraction and must not contain any "fish eyes" during processing.

Owing to the known dependence of the polyolefin morphology on that of the polymerization catalyst and hence on the morphology of the magnesium alkoxide used, it was necessary to provide a process which permits the preparation of spherical, compact particles of magnesium alkoxide having a relatively narrow particle size distribution and a volume average of the particle diameter of less than 10 μm. In particular, in order to ensure freedom from fish eyes and good fluidizability, no significant amount of particles having a diameter greater than about 100 μm must be present, i.e., preferably less than 1%, more preferably less than 0.3% by weight of such particles. This necessitates taking measures to ensure effective atomization on the one hand and to prevent agglomeration of moist particles either in the gas space or on the walls of the preparation apparatus.

The previously unobtainable finely divided magnesium alkoxide free of methoxide groups prepared in this manner can be particularly advantageously used for the preparation of catalysts for liquid-phase polymerization.

In addition to the liquid-phase polymerization of olefins, gas-phase polymerization processes in which the polymerization takes place in, for example, a fluidized bed, have become established worldwide. A catalyst having coarser particles is required for this purpose; mean particle diameters of, for example, 20 μm are typical. A further object of the present invention is therefore to provide a flexible process in which alternatively the finely divided magnesium alkoxide according to the invention, having a volume average particle diameter of less than 10 μm, or a magnesium alkoxide having coarser particles and a volume average of 20 μm or more can be prepared in the same plant without conversion, merely by suitable variation of parameters, such as, for example, load range of the nozzle. Such flexibility of the plant could contribute substantially to its cost-efficiency.

Furthermore, it was an object to provide a simple and rapid process for final drying and decarboxylation of the initially formed finely divided carboxylated magnesium alkoxide.

These objects are achieved in the present invention by the process described below.

The process according to the invention is characterized in that a solution of carboxylated magnesium alkoxide in the same alcohol on which the alkoxide is also based a) is sprayed via a two-material nozzle with internal mixing of the type described in, for example, German Patent 2,627,880, and which is operated in the part-load range at 5 to 30%, preferably 10 to 25%, of capacity, b) into an inert accompanying gas which is under a pressure of 1.0 to 1.2 bar, preferably 1.01 to 1.05 bar, is fed cocurrently and has been preheated to a relatively high temperature of 100° to 140° C., preferably 105° to 120° C., it being advantageous if the spray drier is in the form of a long tube tapering conically downwards, c) after which the resulting finely divided carboxylated magnesium alkoxide is dried and is decarboxylated.

The carboxylated magnesium alkoxide used preferably has the formula $Mg(OR)_2 \cdot x\, CO_2$ where $R = C_2$ to $C_4$, such as, for example, n-propyl, n-butyl, isobutyl or preferably ethyl and $x = 0.2$ to $2.0$. It is prepared in a known manner by dissolving magnesium turnings in the corresponding alcohol and redissolving the initially formed particles of magnesium alkoxide by passing in dry $CO_2$. Here, the $CO_2$ is merely an auxiliary for increasing the solubility of the alkoxide; its reaction with the alkoxide is reversible, and it can therefore be removed again by heating. The larger x, the easier $CO_2$ is released again on heating; it is advisable here to choose x to be only as large as is absolutely necessary, in order to avoid excessive $CO_2$ contamination of the accompanying gas, which is circulated after the alcohol has been condensed out. Specifically, the amount of carbon dioxide used (the value of "x") is that needed to increase the solubility of alkoxide so as to produce solids content enabling spraying through the nozzle with desired sized particles, and may be routinely determined. Where R = ethyl, a value for x of 1.0 to 1.25 is therefore particularly preferred.

The solution may have a solids content of 2 to 40% by weight. Concentrations between 20 and 40% by weight, particularly preferably 25 to 30% by weight, based on dry substance, are usually used.

The nozzle used is a two-material nozzle with internal mixing. Liquid pressure and gas pressure must be the same. Spraying is carried out at pressures between 10 and 80 bar, preferably between 35 and 45 bar.

Any inert gas may be used as the propellant and as the accompanying gas. For practical reasons, dry and oxygen-free nitrogen is used. When carboxylated magnesium ethoxide in ethanol is used, the temperature of the accompanying gas is particularly preferably between 105° and 120° C.

Under these conditions, single-material nozzles give particles which are too coarse. Rotating-disk atomizers, which in principle are more suitable, also give a material which is too coarse. However, very good results are obtained using the two-material nozzles described. Specifically, a first pipe is surrounded on its end by an annular chamber into which a second pipe for the gas empties. The annular chamber is connected by several cross bores with the inside of the first pipe so that its end area functions as a mixing chamber.

The ratio of gas flow to liquid flow is to be proportioned so that a short distance before the discharge from mixing chamber the gas volume portion is between 30 to 80% of the total flow cross section. Further both flows with respective to their relevant variables, especially with respect to their velocity, their pressure and also their temperature are proportioned so that at the end of mixing chamber the characteristic sonic velocity of the two-phase mixture, i.e., the critical flow, is present with maximal possible rate of flow.

At the end of the mixing space, the mixture expands into a space where a low pressure prevails. Sudden changes in pressure performs fine atomization if the mixture is expanded in a gaseous atmosphere.

The spray drier may be in the form of a slim tower which consists of an upper cylindrical part having a diameter-to-length ratio of 0.3 to 0.9, preferably 0.6 to 0.8, attached to said nozzle, and a subsequent conical part. It is preferable that this conical part be longer than the cylindrical part. The accompanying gas is fed in and removed cocurrently, the particles formed being deposited in a suitable apparatus, such as a cyclone or a filter.

By means of this procedure, it is possible to obtain, alternatively, a very finely divided magnesium alkoxide or, if desired, also magnesium alkoxide having coarser particles. Because of the nozzle used, which has a small spray angle, and the geometry of the tower, caking on the walls is greatly suppressed. Particles produced have less than about 0.3 to 1.0% by weight over a diameter of 100 μm. The factors influencing the particle size produced are conventional, and one of ordinary skill in art may easily adjust the particle size to a desired value.

Relatively stringent conditions are possible for the final drying and decarboxylation, since, owing to the good preliminary drying compared with the process disclosed in European Offenlegungsschrift 0,236,082, the danger of caking is substantially lower. Any suitable drying apparatus which is preferably suitable for vacuum operation, such as, for example, paddle driers, tumble driers, rotary kilns, etc., may be used. In general, drying is carried out at temperatures of about 110° to 150° C., for a period of 3 to 10 hours, preferably 4 to 8 hours, with application of slightly reduced pressure, preferably 950 to 980 hPa. Under these conditions, the bound $CO_2$ is effectively removed. A paddle drier having paddles which pass close to the edge or an apparatus which introduces the heat directly into the product is particularly suitable.

The magnesium alkoxide powder obtained in this manner can be converted by all conventional methods of the prior art, as described in, for example, European Offenlegungsschrift 0,238,082, into a catalyst for the polymerization of α-olefins. The polymerization catalyzed therewith can be carried out in any conventional manner.

The resulting finely divided catalyst powder is particularly suitable for liquid-phase polymerization of α-olefins, such as, for example, ethylene, propylene, but-1-ene, hex-1-ene or mixtures thereof, either the liquefied monomer or an inert hydrocarbon being used as a liquid medium. The polymerization can be carried out continuously or batchwise.

It should be noted that both the pulverulent magnesium alkoxide described here and the polymerization catalyst prepared therefrom have different sensitivities to oxygen, moisture, carbon dioxide, acetylenes and sulfur compounds; such catalyst poisons must therefore be carefully excluded during the process.

Polypropylene prepared using such catalysts has a high stereospecificity and a high bulk density and is easily fluidizable during pneumatic conveying, with fluidization beginning at less than 7 cm/sec, typically less than 3 cm/sec and under suitable conditions less than 1 cm/sec. Because of the small particles size, according to the invention, of the catalyst and the absence of coarse particles, the polyolefin has a very low ash content and can be processed without fish eyes.

Figure 1:
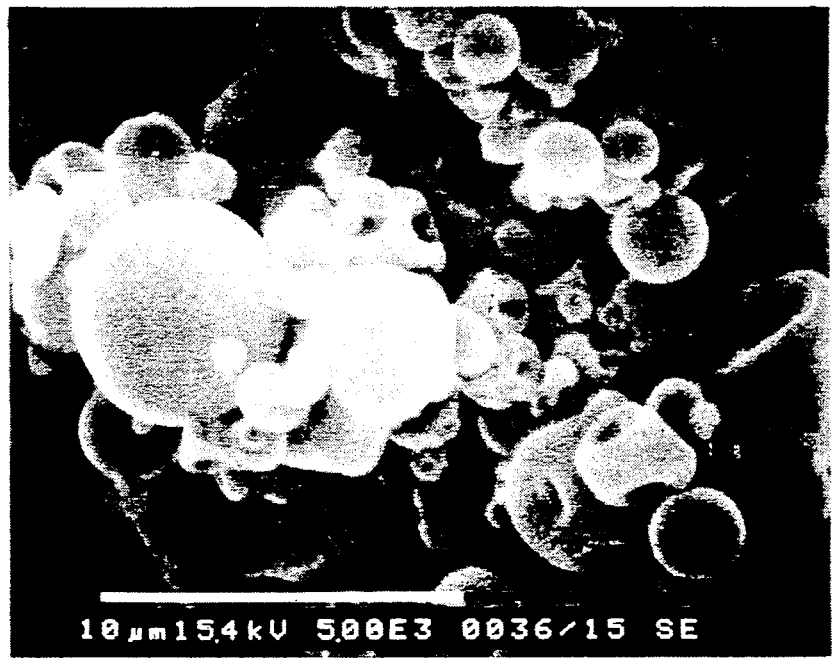
FIG. 1 is a scanning electron micrograph of decarboxylated magnesium ethoxide prepared in Example 3.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 40 00 697.2, filed Jan. 12, 1990, are hereby incorporated by reference.

EXAMPLE 1

Ethanolic solution of carboxylated magnesium ethoxide.

In a 3 $m^3$ stirred container, 300 kg of magnesium ethoxide are added to 1,000 kg of ethanol while stirring, and then 145 kg of $CO_2$ are metered in via a dip tube extending below the liquid surface, in such a way that no gas bubbles appear at the liquid surface. The magnesium ethoxide particles which are virtually insoluble in ethanol, gradually dissolve with reaction with the $CO_2$. A slightly cloudy opalescent solution of 30.8% by weight of carboxylated magnesium ethoxide $Mg(OC_2H_2)_2 \cdot 1.25\ CO_2$ is formed.

EXAMPLE 2

Spraying the solution

In a spray tower in which the cylindrical part has a diameter-to-length ratio of 0.7, 12.3 kg/h of the solution from Example 1 are sprayed by means of a two-material nozzle with internal mixing in accordance with German Patent 2,627,880 (load: 7% of capacity) into an accompanying gas stream (dry $N_2$) heated to 110° C. The drier outlet temperature is about 90° C. The particles are deposited in a double cyclone; the yield is 89.4%, the process being carried out without fine dust filters downstream of the cyclone.

The resulting particles of carboxylated magnesium ethoxide having a weight average particle diameter of 8.4 m (determined by laser diffraction using a "Microtrac" apparatus from Leeds & Northrup). They have the following particle size distribution:

$d_{10}=3.0\ \mu m$; $d_{50}=6.9\ \mu m$; $d_{90}=15.0\ \mu m$; i.e., 10% by weight of the particles having a diameter of up to 3 $\mu m$, etc. The largest diameter measured is 38 $\mu m$.

The residual ethanol content is 4.9% by weight and the $CO_2$ is still bound.

EXAMPLE 3

Drying and decarboxylation 300 g of the product from Example 2 are subsequently dried for 5 hours at a pressure of 980 mbar and an internal temperature of 131° C. in a stream of nitrogen (about 10 l/h) in a 2 l laboratory paddle drier having PTFE paddles which pass close to the edge, a constant weight being achieved.

The primary particles sizes do not change during this procedure; however, small agglomerates form, these being broken up again in stirring during further catalyst preparation. By means of scanning electron micrographs, it is possible to show that the individual spherical particles are not destroyed by the treatment in the paddle drier (see FIG. 1).

The magnesium ethoxide thus obtained is used for the preparation of a catalyst for the polymerization of α-olefins according to European Offenlegungsschrift 0,236,082. The activity and stereospecificity of the catalyst obtained are good; in liquid-phase polymerization of propylene, a polypropylene having high bulk density and good fluidizability is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of finely divided, spherical magnesium alkoxide, consisting of spray drying a solution of a corresponding carboxylated magnesium alkoxide, wherein:

the solution is sprayed in a single step via a two-material nozzle with internal mixing, which is operated in the partial-load range at 5 to 30% of its capacity, into an inert accompanying gas which is fed cocurrently.

2. A process according to claim 1, wherein the magnesium alkoxide has the formula $Mg(OR)_2 \cdot xCO_2$, the solution of magnesium alkoxide is in an alcohol ROH, wherein R is independently $C_{2-4}$-alkyl and x is 0.2 to 2.0, and the inert gas is under a pressure of about 1.0 to 1.2 bar and is preheated to about 100° to 140° C.

3. A process according to claim 1, wherein the solution comprises carboxylated magnesium alkoxide in an alcohol.

4. A process according to claim 1, wherein the magnesium alkoxide has the formula $Mg(OR)_2 \cdot xCO_2$, wherein x=0.2 to 2.0 and R is $C_{2-4}$-alkyl.

5. A process according to claim 1, wherein the solution is sprayed into an inert gas having a temperature of 100°–140° C.

6. A process according to claim 1, wherein the nozzle is operated at 10 to 25% of its capacity.

7. A process according to claim 1, wherein the nozzle is part of a spray drier comprising an upper cylindrical part, attached to said nozzle, said cylindrical part having a diameter-to-length ratio of 0.3 to 0.9, and a subsequent conical part.

8. A process according to claim 7, wherein the conical part of the spray drier is longer than the cylindrical part.

9. A process according to claim 4, wherein R is ethyl.

10. A process according to claim 9, wherein x is 1.0 to 1.25.

11. A process according to claim 1, wherein the gas has a temperature of 105°–120° C., and the solution is magnesium ethoxide in ethanol.

12. A process according to claim 1, wherein the nozzle is part of a spray drier comprising an upper cylindrical part, attached to said nozzle, said cylindrical part having a diameter-to-length ratio of 0.6 to 0.8, and a subsequent conical part.

13. A process for the preparation of finely divided, spherical magnesium alkoxide, consisting of spray drying a solution of a corresponding carboxylated magnesium alkoxide, wherein the solution is sprayed via a two-material nozzle with internal mixing, which is operated in the partial-load range at 5 to 30% of its capacity, into an inert accompanying gas which is fed cocurrently, and further drying the resulting finely divided carboxylated magnesium alkoxide, whereby said magnesium alkoxide is decarboxylated.

* * * * *